(12) United States Patent
Kantarevic

(10) Patent No.: US 8,221,291 B1
(45) Date of Patent: Jul. 17, 2012

(54) ATHLETIC EQUIPMENT INCLUDING A HEALTH AND/OR IMPACT SENSOR

(76) Inventor: Admir Dado Kantarevic, Des Moines, IA (US)

(*) Notice: Subject to any disclaimer, the term of this patent is extended or adjusted under 35 U.S.C. 154(b) by 0 days.

(21) Appl. No.: 12/630,984

(22) Filed: Dec. 4, 2009

Related U.S. Application Data

(63) Continuation-in-part of application No. 12/128,211, filed on May 28, 2008, now abandoned, and a continuation-in-part of application No. 11/536,999, filed on Sep. 29, 2006, now abandoned.

(51) Int. Cl.
*A63B 71/00* (2006.01)
(52) U.S. Cl. .................................................. 482/8
(58) Field of Classification Search ............... 482/1, 8
See application file for complete search history.

(56) References Cited

U.S. PATENT DOCUMENTS

| | | | |
|---|---|---|---|
| 4,761,005 A * | 8/1988 | French et al. | 273/454 |
| 4,824,107 A * | 4/1989 | French | 273/454 |
| 5,195,752 A | 3/1993 | Reeves et al. | |
| 5,471,405 A | 11/1995 | Marsh | |
| 6,349,201 B1 | 2/2002 | Ford | |
| 6,508,747 B1 * | 1/2003 | Cook | 482/83 |
| 6,611,782 B1 * | 8/2003 | Wooster et al. | 702/149 |
| 6,913,559 B2 | 7/2005 | Smith | |
| 6,925,851 B2 | 8/2005 | Reinbold et al. | |
| 2005/0288158 A1 * | 12/2005 | LaTour | 482/81 |
| 2006/0047447 A1 * | 3/2006 | Brady et al. | 702/41 |
| 2006/0058155 A1 * | 3/2006 | Kumar | 482/4 |
| 2007/0270283 A1 * | 11/2007 | Liu | 482/8 |

* cited by examiner

*Primary Examiner* — Loan Thanh
*Assistant Examiner* — Shila Jalalzadeh Abyane
(74) *Attorney, Agent, or Firm* — Zarley Law Firm, P.L.C.

(57) ABSTRACT

Athletic equipment is provided including sensors to monitor the effectiveness and health of the athlete. Contact sensors identify stresses or impacts in real time, and interactively, during the training or competition. Concurrently, a health sensor, obtaining and transmitting indicia corresponding to the physical condition of the athlete (such as heart rate, blood pressure, etc.) can be communicated simultaneously and synchronously with the monitored stress or impact date for use in optimizing athlete performance or monitoring athlete physiology. Such data can be transmitted to a remote location as well. In either case, such information can provide a system for optimizing athlete performance, rather merely tracking historical information. Real time analysis and physiological-performance correlations can be achieved, thereby minimizing the need, or extend of an iterative training regime.

9 Claims, 5 Drawing Sheets

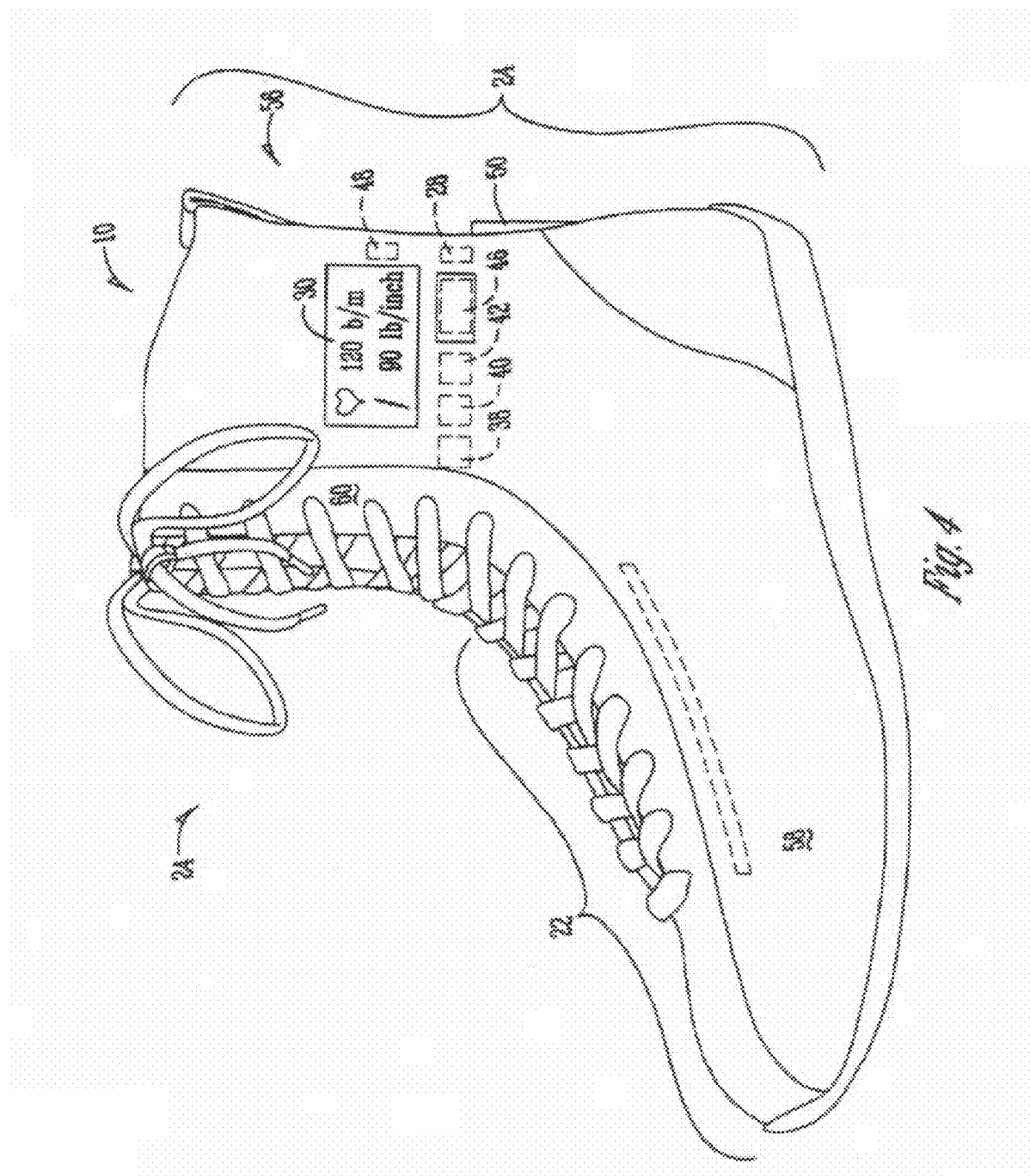

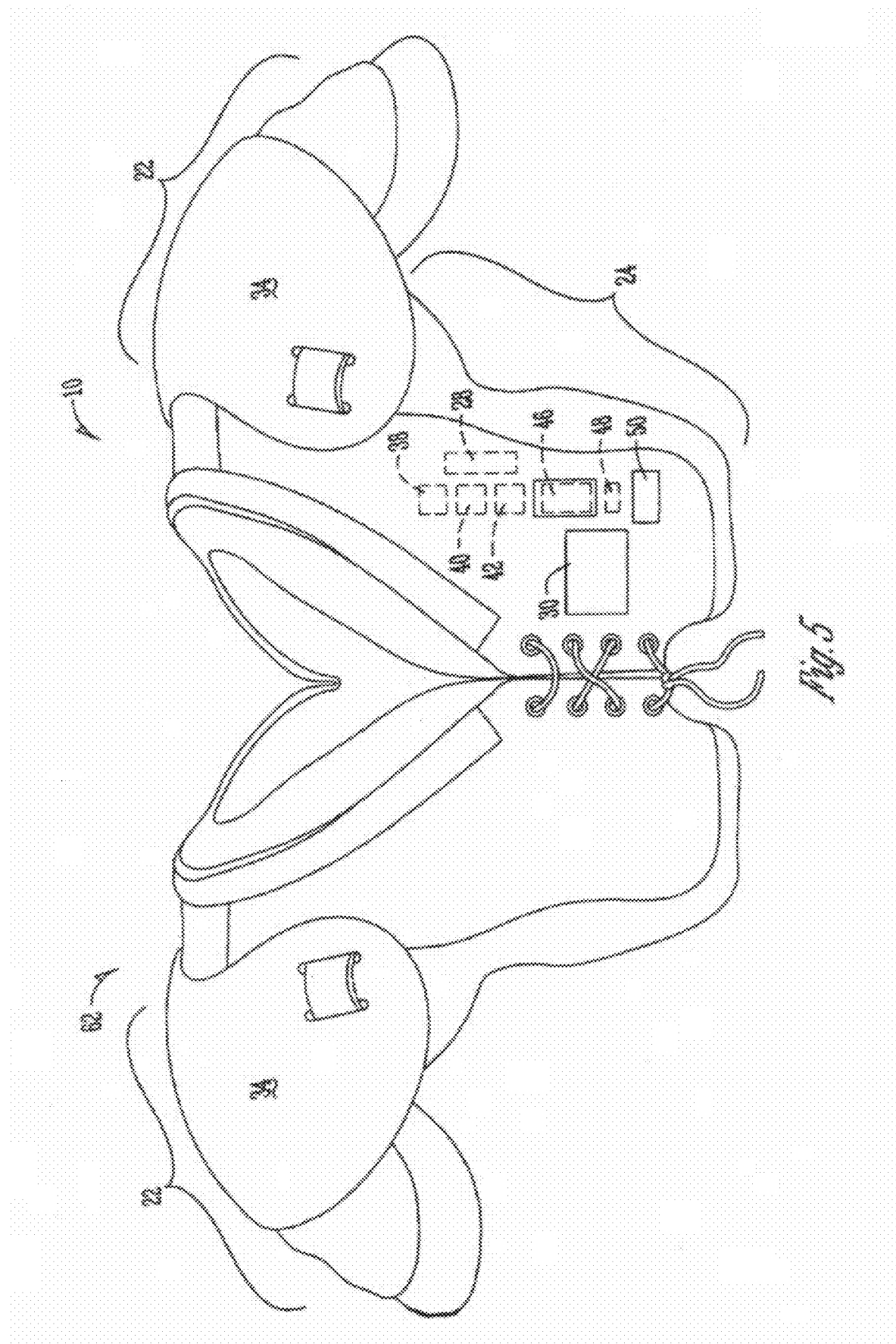

ATHLETIC EQUIPMENT INCLUDING A HEALTH AND/OR IMPACT SENSOR

RELATED APPLICATIONS

The present invention is a Continuation in Part of U.S. patent application Ser. No. 12/128,211, filed on May 28, 2008 now abandoned and U.S. patent application Ser. No. 11/536,999, filed on Sep. 29, 2006 and herein abandoned. The entire contents and disclosure of the '211 and '999 applications are incorporated by reference as if fully rewritten herein.

BACKGROUND OF THE INVENTION

1. Field of the Invention

The present invention relates generally to athletic equipment and, more particularly, to athletic equipment including sensors and feedback monitors to allow the tracking of effectiveness of training and health of the athlete.

2. Description of the Related Art

Typically, many types of sports and training activity require the monitoring of athlete performance. In the many varieties of cardiovascular exercise, the athlete themselves may wish to monitor heart rate in order to maintain the peak benefits of exercise. In contact sports, such as football, boxing, kick boxing, and martial arts, such monitoring is prevented due to the use of protective gear in both competition and training. Such protective gear usually includes some form of padding surrounding an area of the body that is subject to impact. Additionally, the possibility of impact while engaging in such activities poses additional difficulties in monitoring an athlete's physical condition.

Further, many competitive sports include monitoring of athletic performance as a measure of success or for purposes of tracing statistics. The speed of an athlete in the 40-yard dash, or speed of a pitcher's fastball, while determinative of the overall athletic contest, are statistics that enthusiast follow anyway. However, in contact sports, such as football, boxing, kick boxing, and martial arts, such monitoring of the force of any contact is currently not possible and, as such, not available to fans of such activities.

A search of the prior art did not disclose any patents that read directly on the claims of the instant invention; however, the following references were considered related.

U.S. Pat. No. 6,349,201, issued in the name of Ford, discloses a bullet-proof vest with a built-in impact sensor in the exterior layers. Once a hit is detected, the status of the wearer is monitored and a distress signal is remotely transmitted, if necessary. Such a 'garment', however, it not a piece of athletic equipment and is designed not for use in optimizing athlete performance, but rather for passively tracking received impact for circumstantially identifying distress in law enforcement or military personnel.

U.S. Pat. No. 6,913,559, issued in the name of Smith, teaches a weight-lifting glove that has a pressure sensor to monitor the pressure exerted during weightlifting. The force measured is then displayed on an LCD screen. Such a 'garment', however, merely incorporates a load cell to identify the amount of force exerted as an isometric feedback mechanism to replace the use of or emulate the functionality of a separate exercise equipment, and is not designed for use in optimizing athlete performance or monitoring athlete physiology.

U.S. Pat. No. 5,471,405, issued in the name of Marsh, teaches a show with a built-in pressure sensor to measure the forces on the athlete's foot during running. The sensor sends the data to a processor which relays to information to a transmitter for sending to a remote location. Again, such a 'garment', however, it not a piece of athletic equipment and is designed not for use in optimizing athlete performance, but rather merely for tracking a single parameter, impact force between ground and shoe, for the coach to later analyze for purposes of an iterative training regime.

Also, U.S. Pat. No. 5,195,752, issued in the name of Reeves et al. discloses a shirt that can be worn during paint ball games. The shirt has a built-in sensor which detects when the user is hit and displays a message. Again, such a 'garment', however, it not a piece of athletic equipment and is merely a wearable 'target' with a uniquely implemented annunciator.

Finally, U.S. Patent Publication 2006/0047447, published in the name of Brady et al., teaches monitoring athletes performance during a athletic event. Such teachings, however, fail to allow for training in addition to just the event, and requires a computing device outside the ring for read out because of the provision of a readout on the gloves. Additionally, the system taught in this reference requires three types of gloves or monitors as compared to the present invention, in which all are integrated and no outside display computing is required.

In essence, such related art are designed to monitor the performance of the equipment itself, and not physiological performance of the athlete himself. Nor is such equipment adaptable for both monitoring of athlete training, as well as for determination of athlete statistics during competition. Consequently, a need has been felt for providing an apparatus and method of monitoring an athlete's vital signs such as pulse rate, blood pressure, breathing rate, etc. during athletic performance in a manner that is transmittable through audio and/or visual outputs.

SUMMARY OF THE INVENTION

It is a general feature of the present invention to provide improved athletic equipment.

Specifically, it is a feature of the present invention to provide improved athletic equipment including sensors to monitor the effectiveness and health of the athlete. Additionally, it is a further feature of the present invention to provide for monitoring of impact statistics for purposes of comparison or tracking by spectators or judges.

Briefly described according to one embodiment of the present invention, a piece of athletic equipment, such as a glove or boot, is provided for use in athletic competitions. The equipment includes a portion intended for contact with another participant or object and a non-contact portion. The contact portion preferably includes an impact sensor. The impact sensor may be secured to the contact portion by either embedding the sensor within the contact portion or securing the sensor to the surface of the contact portion. In addition, the piece of athletic equipment also includes a health sensor to monitor vital signs of the athlete, such as heart rate and/or blood pressure. The health sensor is preferably secured to the piece of athletic equipment in a non-contact area, or ruggedized to operate while withstanding the shock of impact if secured to the contact area. A method of monitoring is in communication with the health sensor to provide the ability of spectators, judges, or the athlete to see, hear or otherwise track the condition of the athlete, the force of any individual impact, or other metrics of the athletic performance.

In accordance with a preferred embodiment, the impact sensor and health sensor are both operatively connected to a display. Preferably, the display is located on the piece of athletic equipment in a non-contact area such that it can be viewed by the athlete, trainer, coach or medical professional without the need to remove the athletic equipment or to add additional equipment. Alternately, an audible output can allow for monitoring by the athlete as well under circumstances where visual monitoring would distract from performing. In such an embodiment, a display can be adapted to provide audible annunciation corresponding to the physical condition of the athlete and the impact data.

Another preferred embodiment of the present invention may also include a storage device, such as a flash card, memory stick, or other solid state memory device to store the data collected by the impact and/or health sensors. Alternatively, the data collected can be transmitted to a remote location for storage and/or monitoring. A battery, preferably secured to the piece of athletic equipment in a non-contact area, is used to provide the power necessary to amplify, process, store, display and/or transmit the information received from the impact and health sensors.

An advantage of the present invention is that it allows for the convenient monitoring of an athlete's vital sings, such as pulse rate, blood pressure, respiration rate, etc. during the athletic performance.

Another advantage of the present invention is that it is allows for real-time reviewing of this data for the athlete, trainer or spectator.

Yet another advantage of the present invention is that it can store such data for later analysis.

Further, a preferred embodiment of the present invention can transmit such data to a remote receiver for monitoring.

Further still, a variety of sensors, such as impact sensors, accelerometers, and the like can be incorporate in combination with the present invention.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

FIG. 4 is another embodiment of the present invention on another type of athletic equipment, herein a boot; and FIG. 5 is another embodiment of the present invention on another type of athletic equipment, herein a set of shoulder pads

DESCRIPTION OF THE PREFERRED EMBODIMENTS

The best mode for carrying out the invention is presented in terms of its preferred embodiment, herein depicted within the Figures.

1. Detailed Description of the Figures

The present invention will be described as it applies to its preferred embodiment. It is not intended that the present invention be limited to the described embodiment. It is intended that the invention cover all modifications and alternatives which may be included within the spirit and scope of the invention.

Figure 1:
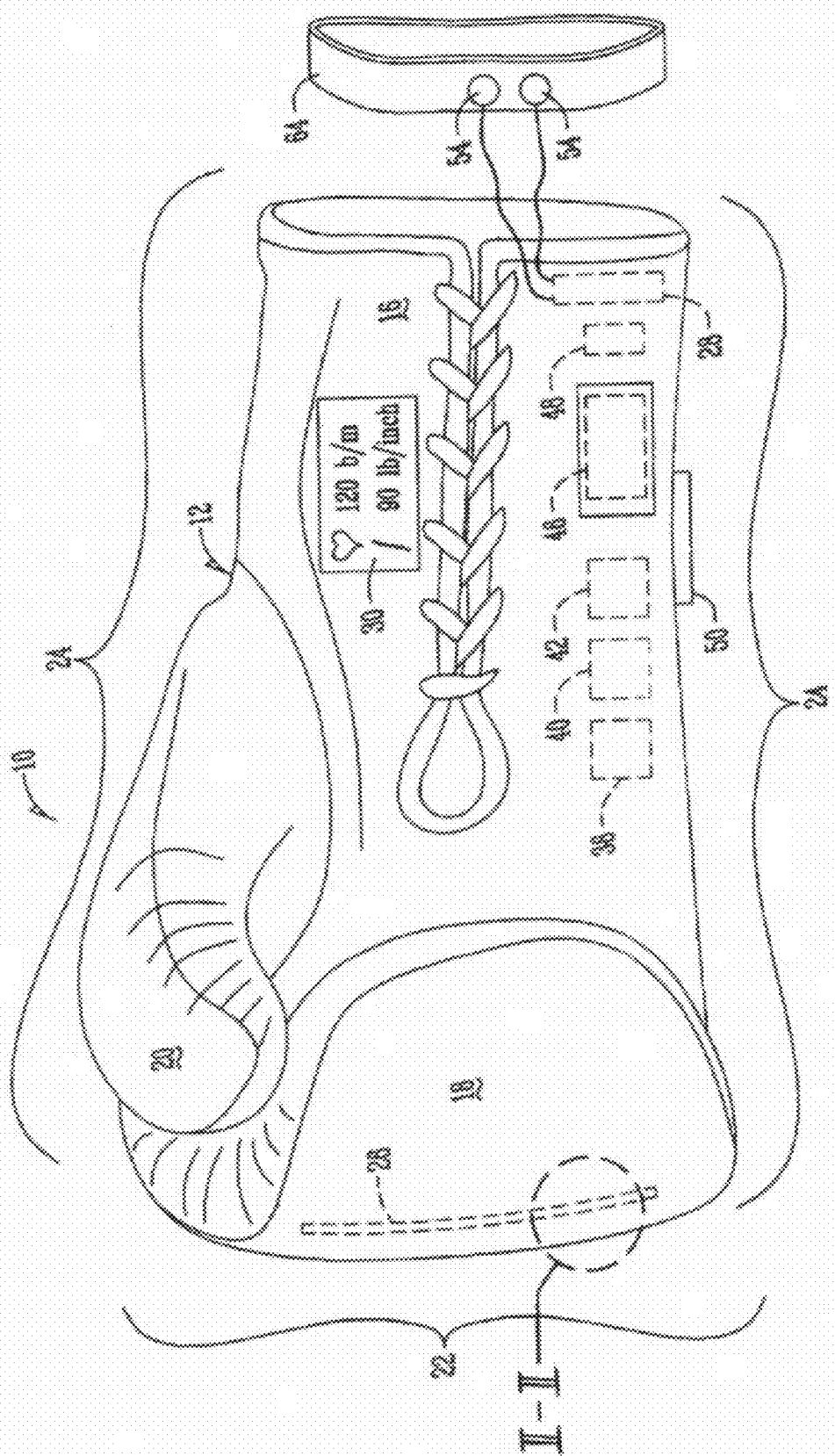
FIG. 1 is a pictorial representation of one type of athletic equipment, here a boxing glove, including many of the features of one embodiment of the present invention.

Now, referring to the drawings, FIG. 1 illustrates a piece of athletic equipment 10. In FIG. 1, the piece of athletic equipment 10 is a boxing glove 12. However, as indicated above, the use of a boxing glove 12 as an embodiment for the piece of athletic equipment 10 is not intended to be limiting, but rather used merely as an example, and it is intended that any piece of athletic equipment 10 can selected for any particular athletic activity and can be adapted for use as described herein. As shown, the body of the boxing glove 12 includes a mitten 14 into which the boxer places his hand and a wrist portion 16 which is used to secure the glove 12 to the boxer. The mitten 14 typically includes a finger portion 18 and a thumb portion 20. In a usual boxing match the finger portion 18 is the area used to strike the athlete's opponent. Thus, in a boxing situation, the finger portion 18 would be the contact portion 22 for this particular piece of athletic equipment 10.

Similarly, since neither the thumb portion 20 nor the wrist portion 16 of the glove 12 are typically used for contacting one's opponent, they may be considered the non-contact portion 24 for this particular piece of athletic equipment 10. The determination of where the contact portion 22 and the non-contact portion 24 are will vary for each particular piece of athletic equipment 10 and may depend on the intended usage of that equipment for the particular sport played.

As shown further in FIG. 1, the boxing glove 12 includes many features of the present invention. Not an of these features need to be included. Instead, the features included will likely depend on the intended use of the particular piece of athletic equipment 10. The features shown include an impact sensor 26 located in the contact portion 22 of the glove 12.

Figure 2:
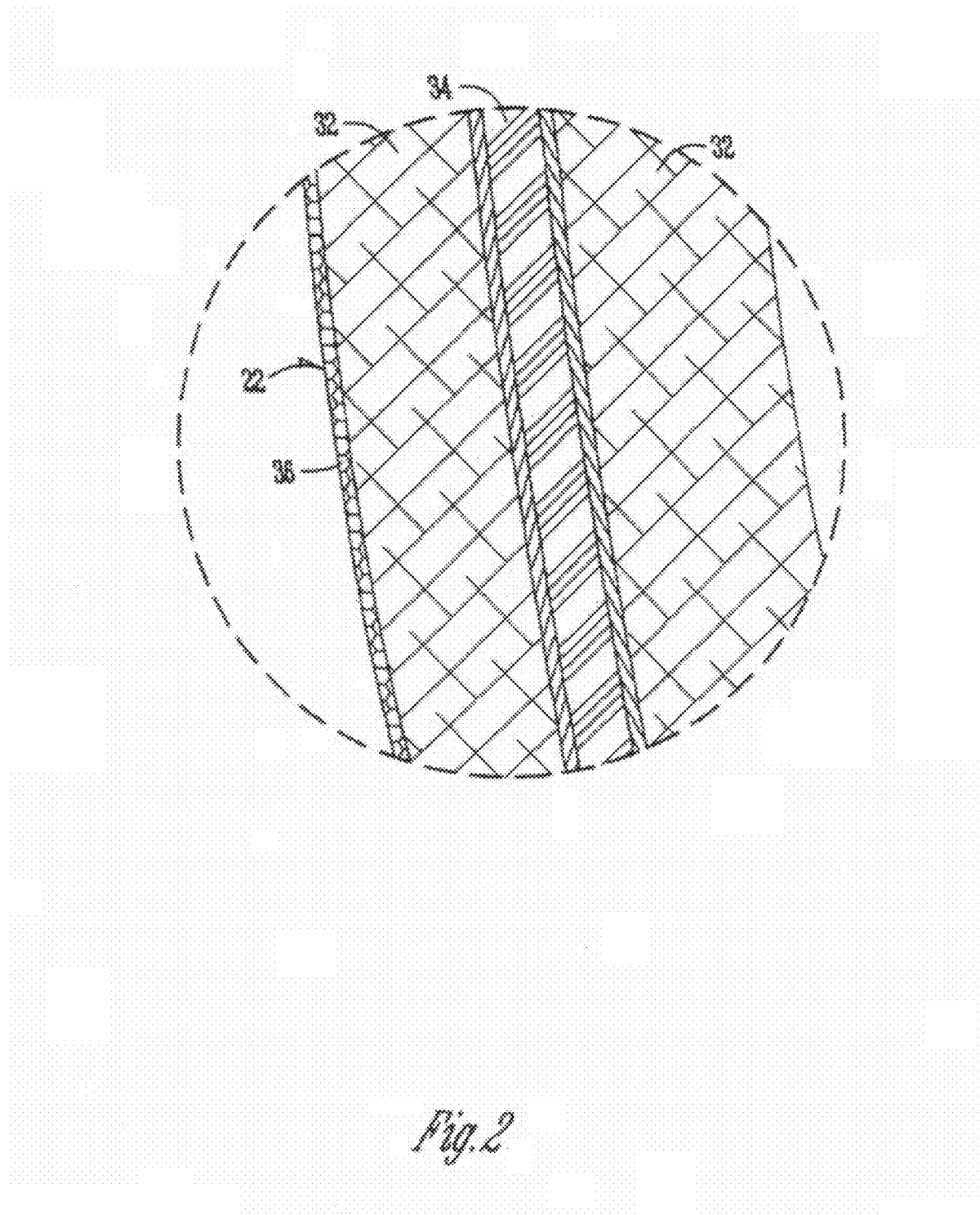
FIG. 2 is a cross sectional view of section II-II from FIG. 1 showing one embodiment of the impact sensor in the contact portion of a piece of athletic equipment.

As can be seen in FIG. 2, it is preferred that the impact sensor 26 be located within the glove 12 and behind substantial padding 32. The location of the impact sensor 26 may vary according to the desired use. If desirable, the impact sensor 26 may be located 5 on the exterior of the glove 12 on top of the padding 32 and any coating 36 that may be present. The impact sensor 26 may be secured with glue, stitching or any other known means. Locating the sensor 26 behind substantial padding 32 within the glove 12 minimizes the potential for the sensor's presence to be felt by an opponent. Preferably, padding 32 is placed on both sides of the impact sensor 26 to minimize any potential for injury caused by contacting the sensor 26 during an impact such as a punch.

Figure 3:
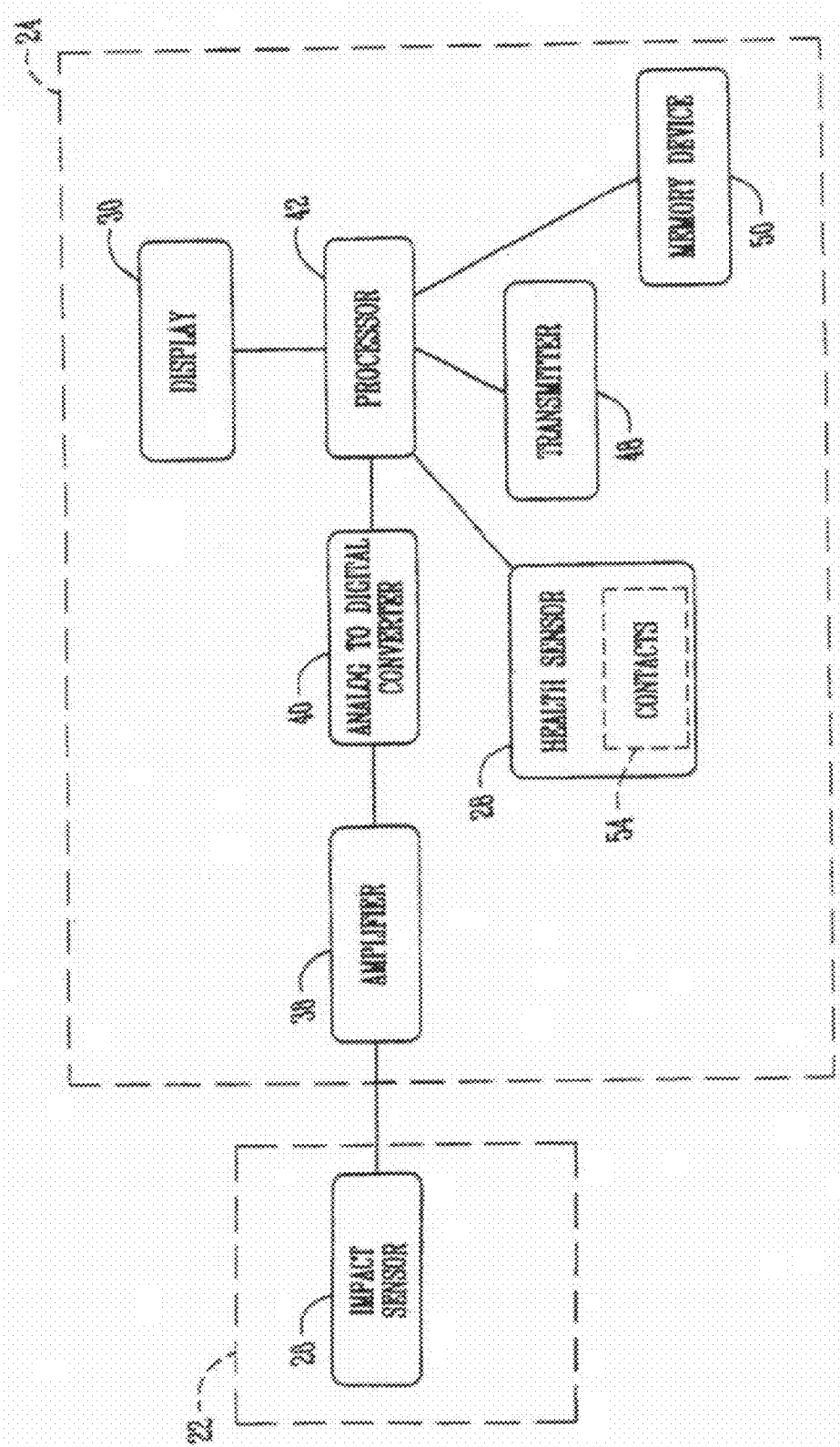
FIG. 3 is a block diagram illustrating details of the electrical circuitry incorporated in the embodiment of the invention shown in FIG. 1.

The impact sensor 26 is preferably a film of piezoelectric material of minimal thickness. This type of impact sensor 26 may be mounted on either a flexible or rigid substrate, if necessary, depending on the application. Other types of impact sensors may be used, such as accelerometers or pressure sensors. As shown in FIG. 3 and using the piezoelectric film material of the preferred embodiment, the impact sensor 26 is operatively connected by wiring to an amplifier 38. The amplifier 38 increases the signal produced by the impact sensor 26 to ensure the signal is distinguishable from any electrical noise that may be present. After amplification, the signal is transmitted to an analog to digital converter 40 and sent to a processor 42. The processor 42 converts the signal to a force value.

The electric signal produced by the impact sensor 26 of the preferred embodiment will have an amplitude that is a function of the force of the blow. The value of this amplitude is received by the processor 42 which converts the amplitude to a force value. This force value is then preferably sent to a display 30.

The display 30 is preferably a LED display that is sewn into the wrist portion 16 or other non-contact portion 24 of the glove 12. The display 30 may also be a flexible display such as that made by Koninklijke Philips Electronics. Alternatively, the display 30 made be made from OLEDs, a plasma display, E-INK™ or any other suitable known technology.

The display 30, processor 42, analog to digital converter 40 and amplifier 38 may all be powered by a battery 46. Preferably, the battery 46 is a rechargeable lithium-ion battery which is removably secured to the non-contact portion 24 of the glove 12. The battery 46 may also be used to power a radio frequency or BLUETOOTH™ transmitter 48. The transmitter 48 is located in the non-contact portion 24 of the glove 12 and sends signals to a receiver (not shown) which may be connected to a computer or any other system to monitor the athlete during a competition. The transmitter may be set to send signals via a unique radio frequency or to send an identification signal to the receiving device. This allows receiving device to differentiate between contestants.

Other functionality is further intended through the transmission of information through this radio frequency or BLUETOOTH™ signal. One anticipated use is for the communication with the health sensor to provide the ability of spectators, judges, or the athlete to see, hear or otherwise track the condition of the athlete, the force of any individual impact, or other metrics of the athletic performance. Another anticipated use is to provide for an audible monitoring of this data to the athlete himself or herself in situations where this feedback would be useful, yet the visual monitoring of an athlete's vital signs such as pulse rate, blood pressure, breathing rate, etc. during training or the athletic performance on the display 30 is impeded by the athlete's activities. In such an embodiment, the display 30 is adapted to provide audible annunciation corresponding to the physical condition of the athlete and the impact data.

A storage or memory device 50 is also connected to the processor 42. The memory device 50 is preferably a removable device such as a memory stick or flash card. The memory device 50 will store information from the processor for later use. This enables the athlete, trainer, coach or other interested party to evaluate the athlete's performance after a competition, workout, or training exercise.

Preferably, the glove 12 also includes a health sensor 28 which monitors one or more, vital signs of the athlete. This health sensor 28 may be powered by the battery 46 if necessary. For example, the health sensor 28 could be a heart rate monitor that is connected to one or more contacts 54 on the interior surface of the wrist portion 16 of the glove 12. As is shown in FIG. 1, the contacts 54 may be contained on a wristband 64 that is wired or otherwise operatively connected to the health sensor 28. This allows the contacts to be placed on the wrist or other pulse point of the athlete and also allows the athlete to wrap his hand in a traditional manner.

These contacts 54 use electrical signals to monitor the heart rate of the athlete while the athlete is wearing the gloves 12. This is typically known as electrocardiography. The heart rate or health sensor 28 sends signals to the processor 42 for conversion into a number such as beats per minute. This information may be displayed on the piece of athletic equipment 10 via the display 30, sent to a remote location for monitoring or analysis via the transmitter 48 or may be stored for later analysis on the memory device 50. The health sensor 28 and processor 42 may also include various alarm features, such as when the athlete reaches a maximum allowable heart rate or blood pressure. This alarm may sound through either a build in speaker (not shown) or external speaker or annunciator.

Generally, the features of the present invention have been described for use in association with a boxing glove 12. FIGS. 4 and 5 show the application of many of these features to other forms of athletic equipment 10. FIG. 4 shows where an impact sensor 26, health sensor 28 and display 30 may be located on a users's boot 56. This may be useful in evaluating the performance of soccer players, football kickers, etc. Alternatively, FIG. 5 shows where an impact sensor 28 and display 30 may be located on a set of shoulder pads 62. Shoulder pads 62 equipped in such a manner may be used to evaluate the effectiveness of a block, tackle or 'hit' during a football game. These sensors may also be placed within athletic clothing as well, such as headbands, wristbands, etc.

2. Operation of the Preferred Embodiment

In operation, the present invention can be adapted to incorporate the use of both contact sensors and health sensors into the protective equipment or garments used in contact sports such as football, boxing, kick boxing, and martial arts in both competition and training. Since the protective gear usually includes some form of padding surrounding an area of the body that is subject to impact, the identification of the stresses or impacts can be made and monitored in real time, and interactively, during the training or competition. Concurrently, a health sensor, obtaining and transmitting indicia corresponding to the physical condition of the athlete (such as heart rate, blood pressure, etc.) can be communicated simultaneously and synchronously with the monitored stress or impact date for use in optimizing athlete performance or monitoring athlete physiology. Such data can be transmitted to a remote location as well. In either case, such information can provide a system for optimizing athlete performance, rather merely tracking historical information. Real time analysis and physiological-performance correlations can be achieved, thereby minimizing the need, or extend of an iterative training regime.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be limited only by the following claims.

Having thus described the invention what is claimed as new and desired to be secured by Letters Patent is as follows:

1. A combination athlete and athletic performance monitoring mechanism to simultaneously monitor the effectiveness of the athletic activity and the health of an athlete, comprising:
    a glove otherwise associated with a selected sporting or training activity that is in physical connection with a portion of an athlete, said glove having a contact area and a non-contact area;
    said contact area housing an impact sensor;
    at least one health sensor located in or on said non-contact area, said health sensor capable of obtaining physiological data that corresponds to the physical condition of said athlete and transmitting said data;

an amplifier operatively connected to and in electronic communication with said impact sensor, said amplifier is configured to increase a signal produced by said impact sensor of sufficient gain to be distinguishable from any electrical noise that may be present;

an analog to digital converter and a processor operatively connected to and in electronic communication with said amplifier for generating a digital signal that relates to a force value applied to said impact sensor; and an externally perceptible output display on the glove for receiving said digital signal from said impact sensor and said physiological data from said at least one health sensor and transmitting and presenting output corresponding to the physical condition of the athlete simultaneously and synchronously with the impact data; and a memory device removably engaged and directly secured along an outer surface of the glove that stores the physiological data and the impact data.

2. The mechanism of claim 1, wherein said impact sensor is located within the interior of said piece of athletic equipment, underneath padding; and further comprising a coating covering said impact sensor.

3. The mechanism of claim 2, wherein said impact sensor comprises a film of piezoelectric material mounted on a substrate.

4. The mechanism of claim 2, wherein said impact sensor comprises an accelerometer.

5. The mechanism of claim 2, wherein said impact sensor comprises a pressure sensor.

6. The mechanism of claim 1, wherein said display is selected from the group comprising: an LED display; a flexible display; an OLED display; a plasma display; and an E-Ink display.

7. The mechanism of claim 1, wherein said health sensor is capable of monitoring one or more vital signs of said athlete.

8. The mechanism of claim 1 wherein the memory device is a memory stick.

9. The mechanism of claim 1 wherein the memory device is a flash card.

* * * * *